«12» United States Patent
Menegatti et al.

(10) Patent No.: US 7,781,489 B2
(45) Date of Patent: Aug. 24, 2010

(54) MICROEMULSIONS OF RETINOIDS, AND PHARMACEUTICAL COMPOSITIONS CONTAINING THEM

(75) Inventors: Enea Menegatti, Abano Terme (IT); Rita Cortesi, Abano Terme (IT); Elisabetta Esposito, Abano Terme (IT); Pierangelo Bellato, Abano Terme (IT); Giovanni Gennari, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 68 days.

(21) Appl. No.: 10/575,616

(22) PCT Filed: Oct. 8, 2004

(86) PCT No.: PCT/EP2004/011236

§ 371 (c)(1),
(2), (4) Date: Apr. 13, 2006

(87) PCT Pub. No.: WO2005/039532

PCT Pub. Date: May 6, 2005

(65) Prior Publication Data

US 2007/0134276 A1    Jun. 14, 2007

(30) Foreign Application Priority Data

Oct. 17, 2003  (IT)  .......................... MI2003A2019

(51) Int. Cl.
*A61K 31/07*  (2006.01)
*A61K 47/36*  (2006.01)

(52) U.S. Cl. ...................................... 514/725; 514/777
(58) Field of Classification Search ................ 514/725, 514/777
See application file for complete search history.

(56) References Cited

U.S. PATENT DOCUMENTS

| 5,023,271 | A | | 6/1991 | Vigne et al. |
| 5,055,303 | A | * | 10/1991 | Riley, Jr. ..................... 424/436 |
| 5,744,155 | A | * | 4/1998 | Friedman et al. ............ 424/434 |
| 5,925,626 | A | * | 7/1999 | della Valle et al. ............ 514/54 |
| 6,551,605 | B2 | * | 4/2003 | Bonda ........................ 424/401 |
| 2002/0102280 | A1 | | 8/2002 | Anderson |
| 2002/0183394 | A1 | | 12/2002 | Gupta et al. |
| 2005/0031547 | A1 | * | 2/2005 | Tamarkin et al. .............. 424/45 |

OTHER PUBLICATIONS

Smolinkse, S., Handbook of Food, Drug, and Cosmetic Excipients, 1992, CRC Press, 1st ed., p. 251.*
Cevc, G. Advanced Drug Delivery Reviews, 2004, 56, p. 675-711.*
Entry for microemulsions, Encyclopedia of Chemical Physics and Physical Chemistry, 2001, Institute of Physics Publishing, http://ww0.knovel.com/, accessed online on Jul. 2, 2008.*
Patent Abstracts of Japan, vol. 011, No. 232 (C-437), Jul. 29, 1987 & JP 62 045336 A (Toyo Biyuut KK), Feb. 27, 1987 abstract.
Patent Abstracts of Japan, vol. 2000, No. 10, Nov. 17, 2000 & JP 2000 204011 A (Human Limited:KK), Jul. 25, 2000 abstract.

* cited by examiner

*Primary Examiner*—Shaojia Anna Jiang
*Assistant Examiner*—Jonathan S Lau
(74) *Attorney, Agent, or Firm*—Young & Thompson (57) ABSTRACT

Disclosed are water-in-oil (W/O) microemulsions containing as active ingredient a retinoid, a phospholipid emulsifier, and possibly hyaluronic acid or salts thereof.

15 Claims, 6 Drawing Sheets

MICROEMULSIONS OF RETINOIDS, AND PHARMACEUTICAL COMPOSITIONS CONTAINING THEM

This invention relates to water-in-oil (W/O) microemulsions containing a retinoid as active ingredient, a phospholipid emulsifier, and possibly hyaluronic acid or salts thereof.

BACKGROUND TO THE INVENTION

Retinoids are defined as a series of compounds which are natural derivatives or synthetic analogues of vitamin A. The role of vitamin A as an essential nutrient was recognised as early as 1913, since which time a great deal of research has been conducted on the product. Wolbach and Howe (J. Exp. Med. 42: 753,1925) first described the histopathological epithelial variations caused by vitamin A deficiency in 1925. This led to the identification of retinol and other natural analogues which began to be used, on a purely empirical basis, as chemopreventive agents of neoplastic transformation.

The role of retinoids in oncological chemoprevention was endorsed by the publication of various epidemiological studies which demonstrated that a regular vitamin A intake was significantly correlated with a lower incidence of tumours, especially lung cancer (Zeigler R. G. et al., Cancer Causes and Control 7: 157-177, 1996; Krishnan K. et al., Primary Care 25: 361-382, 1998).

Only some of the over 4000 retinoids tested to date have a sufficiently favourable therapeutic efficacy/toxicity ratio to allow their clinical use. The relatively recent discovery of nuclear receptors for retinoic acid (which belong to two distinct types, called RAR and RXR) has considerably improved knowledge of their action mechanisms.

Numerous clinical trials have been conducted with retinoids, many of them on skin diseases such as lichen planus and leucoplakia which, due to the high frequency of neoplastic transformation, are classed as pre-cancerous lesions (Hong W et al., N. Engl. J. Med 315: 1501-1505, 1986; Lippman S. M et al., N. Engl. J. Med 328: 15-20, 1993).

At present, the internationally recognised clinical use of the retinoids relates to the treatment of acute promyelocytic leukemia and skin diseases with a hyperproliferative component such as acne and psoriasis.

Fenretinide (4-hydroxyphenyl retinamide) is a semi-synthetic retinoid which was developed as a chemoprotective agent (Costa A. et al., Ann. N.Y. Acad. Sci. 768: 148-162, 1995; Pienta K. J. et al., Am. J. Clin. Oncol. 20: 36-39, 1997).

Unlike other natural retinoids such as all-trans, 13-cis- and 9-cis-retinoic acid, fenretinide does not induce any systemic catabolism which could interfere with the long-term maintenance of pharmacologically useful plasma concentrations. This characteristic, combined with the low toxicity of the product and its ability to inhibit some phenomena associated with carcinogenesis, provides the rationale for the development of fenretinide as a chemoprotective agent in neoplastic disorders such breast, prostate and bladder cancer.

Other phase II trials, conducted on a limited number of subjects, have evaluated the effect of fenretinide on patients suffering from prostate cancer (Pienta K. J. et al., Am. J. Clin. Oncol. 20: 36-39, 1987), melanoma (Modiano M. R. et al., Invest. New Drugs 8: 317-319, 1990) and myelodysplastic syndromes (Garewal H. S. et al., Leukemia Res. 13: 339-343, 1989). However, the results of these studies were rather disappointing, whereas chemoprevention studies conducted on patients suffering from leucoplakia or lichen planus (dermatological lesions which often present neoplastic degeneration) have given promising results (Tradati N. et al., Canc. Letters 76: 109-111, 1994).

In these cases the patients were treated topically, with the result that the fenretinide concentrations reached in the lesion were probably similar to, if not higher than those which have proved active in vitro.

At present, topical formulations of retinoids are mainly presented in the form of creams with a fatty base or gels. DE 19946184 describes emulsions of retinoids characterised by a continuous aqueous phase, a mainly non-crystalline viscous oily phase, and a mixture of emulsifiers. Microemulsions of active ingredients which are poorly soluble in water and can be administered by the parenteral, topical or oral route are described in WO 99/56727, EP 211258 and EP 760237.

Topical formulations of retinoids in the form of microemulsions (macroscopically monophasic dispersed systems constituted by at least three components, such as an oily phase, an aqueous phase and a surfactant) are not available. The main chemico-physical properties of microemulsions which characterise their particular structure are transparency, isotropy and thermodynamic stability. As a result of these characteristics, microemulsions are of considerable interest to the pharmaceutical industry. In fact:

(a) the particular microstructure of microemulsions enables molecules with different chemico-physical characteristics to be solubilised;

(b) the transparency of the system makes it possible to check that the active ingredients are completely solubilised;

(c) thermodynamic stability entails major advantages, as the systems obtained are stable for long periods of time.

A further advantage of the topical use of microemulsions is the possibility of increasing the rate of penetration of the active ingredients through the stratum corneum.

Drug release is known to be much faster when gel microemulsions are used rather than conventional formulations (Martini M. et al., J. Pharm. Belg. 39, 348-354, 1984; Ziegerneyers J. et al., Acta Pharm. Technol. 26, 273-275, 1980; Ziegenmeyers J. et al., Deuxième Congrès International de Technologie Pharmaceutique 3, pp. 235-238, 1980).

Phospholipids have been used as emulsifying agents to stabilise microemulsions: phosphatidylcholines in an organic solvent (50-250 mM) form small inverse micelles which, on the addition of water, undergo one-dimensional growth, until the formation of a kind of three-dimensional network consisting of a tangle of long, flexible cylindrical structures (Luisi et al., Colloid Polym. Sci. 268, 356-374, 1990).

The presence of water causes a drastic increase in viscosity, leading to the formation of a gelified transparent system, the viscosity of which depends on the content of the aqueous phase. The water content, which is consequently a very important factor in the formation of these particular microemulsions, is expressed by the ratio between the water concentration and the molar lecithin concentration:

$$[W]/[lec]=[molar\ water\ concentration]/[molar\ lecithin\ concentration]$$

The maximum value of $[W]/[lec]$ for each microemulsion depends on the type of organic phase used and the lecithin concentration. The maximum viscosity of lecithin-based gel microemulsions is usually obtained after the addition of less than 10 molecules of water per molecule of lecithin, namely at values of $[W]/[lec]<10$.

Gel microemulsions based on soy phosphatidylcholine possess all the characteristics of transparency, thermodynamic stability and isotropy typical of microemulsions (Scartazzini R. et al., J. Phys. Chem. 92, 829-833, 1988; Luisi et al., Colloid Polym. Sci. 268, 356-374, 1990; Lawrence et al., Advanced Drug Delivery Reviews 45, 89-121, 2000).

Phosphatidylcholine is a natural surfactant, and is highly biocompatible (Dreher et al., Skin Pharmacology 9, 124-129, 1996).

Hyaluronic acid (HA) is a heteropolysaccharide composed of alternate residues of D-glucuronic acid and N-acetyl-D-glucosamine. It is a linear-chain polymer with a molecular weight ranging between 50,000 and $13 \times 10^6$ Da, depending on the source from which it is obtained and the preparation methods used. It is found in nature in pericellular gels, in the ground substance of the connective tissue of vertebrates (of which it is one of the main components), and in synovial (joint) fluid, vitreous humour and the umbilical cord.

HA plays an important role in biological organisms, as a mechanical support for the cells of many tissues such as skin, tendons, muscles and cartilage.

It is the main component of extracellular matrix, and also performs other functions such as tissue moisturising and cell lubrication, migration and differentiation.

In view of its properties of bio- and mucoadhesion and its tissue compatibility characteristics, hyaluronic acid and its salts, in particular sodium, potassium, magnesium and calcium salts, possibly suitably fractionated and/or derivatised, have been proposed as systems for the release of drugs and the preparation of surgical aids, implants, prostheses and the like.

BRIEF SUMMARY OF THE INVENTION

It has now been found that retinoids can be advantageously formulated in water-in-oil (W/O) microemulsions using phospholipid emulsifiers, in particular soy phosphatidylcholine and soy lecithin, possibly with the addition of hyaluronic acid or salts and fractions thereof.

The present invention relates to water-in-oil microemulsions containing a retinoid and a phospholipid emulsifier as an active ingredient. The phospholipid emulsifier is selected from soy phosphatidylcholine and soy lecithin.

The microemulsions of the invention provide better bioavailability than conventional formulations.

The oily phase is preferably constituted by alkyl esters of $C_{10}$-$C_{22}$ fatty acids.

Isopropyl palmitate is particularly preferred.

Retinoids which can be conveniently formulated in the microemulsions according to the invention include isotretinoin (13-cis-retinoic acid), tazarotene and, in particular, fenretinide.

It has also surprisingly been found that the addition of hyaluronic acid (HA), possibly salified, and in particular sodium hyaluronate or HA derivatives, to microemulsions further increases the bioavailability of the active ingredient.

The HA used in the present invention may derive from any source, such as extraction from rooster combs (EP 0138572), fermentation (EP 0716688), or technological means (Italian patent application no. PD94A000042), and have a molecular weight of between 400 and $3 \times 10^6$ Da, in particular between 400 and $1 \times 10^6$ Da, and even more particularly between 400 and 200,000 Da.

The HA derivatives which can be used are listed below:

1) HA salified with organic and/or inorganic bases having a molecular weight of 50-730 KDa (EP0138572) or a high molecular weight (750-1230 KDa, EP 535200);

2) Hyaff: HA esters with alcohols of the aliphatic, araliphatic, cycloaliphatic, aromatic, cyclic and heterocyclic series, with an esterification percentage which may vary, depending on the type and length of the alcohol used (EP 216453);

3) Hyadd: HA amides with amines of the aliphatic, araliphatic, cycloaliphatic, aromatic, cyclic and heterocyclic series (EP 1095064);

4) O-sulphated HA derivatives up to the 4th degree of sulphation (EP 0702699);

5) ACP: inner esters of HA (EP 0341745).

The fraction known as Hyalastine, a fraction of hyaluronic acid with molecular weights of between 50 and 200 kDa, is preferred.

Hyaluronic acid and its salts act as viscosity agents, and guarantee improved characteristics in terms of stability and bioavailability.

The microemulsions according to the invention may also contain antioxidants and preservatives such as α-tocopherol, alkyl parabens, and other excipients of conventional use.

The weight percentage of active ingredient can range between 0.01% and 0.5%, preferably between 0.05 and 0.15%, while the weight percentage of lecithin or phosphatidylcholine is typically between approx. 10% and approx. 15%. The aqueous phase typically constitutes approx. 0.5 to 2% in weight of the total microemulsions. Sodium hyaluronate can be added as viscosity agent in percentages of between 0.001 and 0.01% in weight.

The microemulsions according to the invention can be prepared by a process which comprises the addition of a solution of phospholipid emulsifier in the oily phase to the retinoid solution in the same oily phase, and subsequent addition of an aqueous solution possibly containing hyaluronic acid, its salts or derivatives, preservatives, EDTA and other ingredients.

EXAMPLES 1-3

Fenretinide Microemulsions

Preparation Method

α-tocopherol is solubilised in a small volume of isopropyl palmitate (IPP). Soy phosphatidylcholine is solubilised in the remaining volume of isopropyl palmitate at 70° C. under stirring until a clear, transparent solution is obtained.

Propyl paraben is then added, and stirring is continued until solubilisation is complete.

The solution is cooled, the solution of α-tocopherol in isopropyl palmitate is added, and the resulting solution is mixed under gentle stirring.

The active ingredient is solubilised in the resulting solution.

Methyl paraben is solubilised in purified water at 80° C. to prepare the aqueous phase. The solution is cooled at room temperature, and tetrasodium EDTA and hyaluronic acid sodium salt are solubilised under stirring.

The aqueous solution is added to the isopropyl palmitate oily solution, and the resulting system which is initially turbid, is maintained under stirring until a clear, transparent emulsion of acquired viscosity is obtained.

Qualitative and Quantitative Compositions The compositions of the microemulsions obtained by the method described above, which have different W]/[lec] ratios depending on whether they contain sodium hyaluronate, are reported below:

Example 1

IPP2 Hyal ([W]/[lec]: 2)

| Constituent | % w/w | Function |
|---|---|---|
| Fenretinide | 0.05-0.10-0.15 | Active ingredient |
| Phosphatidylcholine | 14.756 | Surfactant |
| Isopropyl palmitate | q.s. for 100 | Oily phase |
| Purified water | 0.7644 | Aqueous phase |
| Hyaluronic acid sodium salt (Hyalastine fraction) | 0.0072 | Viscosity agent |
| α-Tocopherol | 0.10 | Antioxidant |

Example 2

IPP3C Hyal ([W]/[lec]: 3)

| Constituent | % w/w | Function |
|---|---|---|
| Fenretinide | 0.05-0.10-0.15 | Active ingredient |
| Phosphatidylcholine | 14.567-14.560-14.553 | Surfactant |
| Isopropyl palmitate | q.s. for 100 | Oily phase |
| Purified water | 1.1107-1.1102-1.1096 | Aqueous phase |
| Hyaluronic acid sodium salt (Hyalastine fraction) | 0.0108 | Viscosity agent |
| α-Tocopherol | 0.10 | Antioxidant |
| Methyl paraben | 0.00162 | Preservative |
| Propyl paraben | 0.000215 | Preservative |
| Tetrasodium EDTA | 0.00108 | Complexing agent |

Example 3

IPP3C' Hyal ([W]/[lec]: 3)

| Constituent | % w/w | Function |
|---|---|---|
| Fenretinide | 0.05-0.10-0.15 | Active ingredient |
| Phosphatidylcholine | 14.567-14.560-14.553 | Surfactant |
| Isopropyl palmitate | q.s. for 100 | Oily phase |
| Purified water | 1.109-1.108-1.1096 | Aqueous phase |
| Hyaluronic acid sodium salt (Hyalastine fraction) | 0.0108 | Viscosity agent |
| α-Tocopherol | 0.10 | Antioxidant |
| Methyl paraben | 0.00216 | Preservative |
| Propyl paraben | 0.01684 | Preservative |
| Tetrasodium EDTA | 0.00108 | Complexing agent |

Example 4

Rheological Characterisation

Dynamic viscosity measurements were performed to characterise the gel microemulsions produced; in particular, viscosity measurements were conducted by applying increasing shear rate values, from which the viscosity values at a shear rate of a 70 s$^{-1}$ were extrapolated (measurements conducted at 25° C.).

Figure 1:
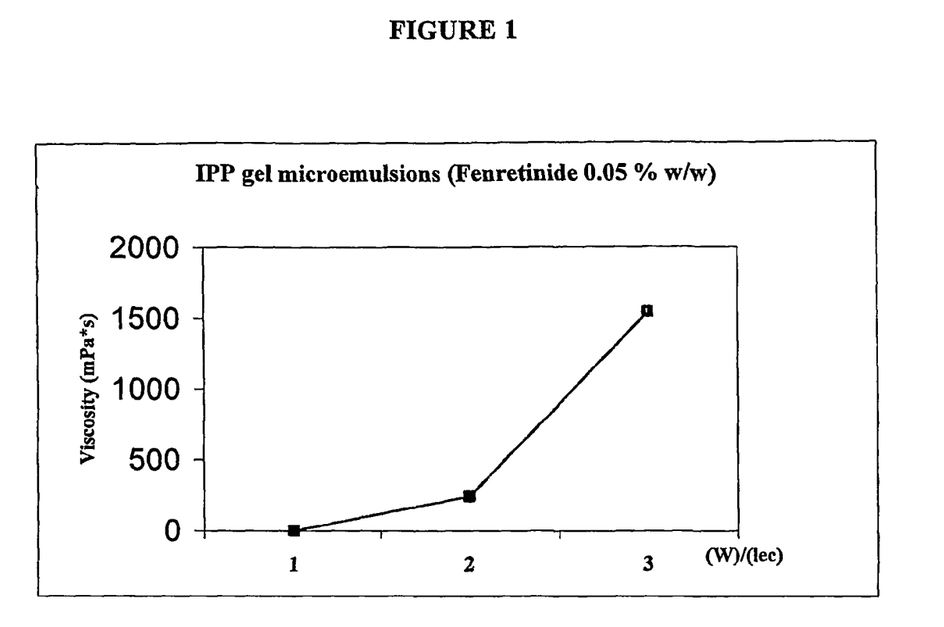
FIG. 1 depicts the viscosity trend of gel microemulsions based on isopropyl palmitate (IPP) at an active ingredient (fenretinide) concentration of 0.05% w/w, depending on the water content ([W]/[lec] equal to 1, 2 and 3).

FIG. 1 shows the viscosity trend of gel microemulsions based on isopropyl palmitate (IPP) at an active ingredient (fenretinide) concentration of 0.05% w/w, depending on the water content ([W]/[lec] equal to 1, 2 and 3).

The viscosity of IPP1 ([W]/[lec]=1) and IPP2 ([W]/[lec]=2) gel microemulsions is considered too low; however, IPP3 gel microemulsions (those with a water content expressed by a [W]/[lec] ratio of 3) are considered to have good viscosity and consistency characteristics for topical application.

Figure 2:
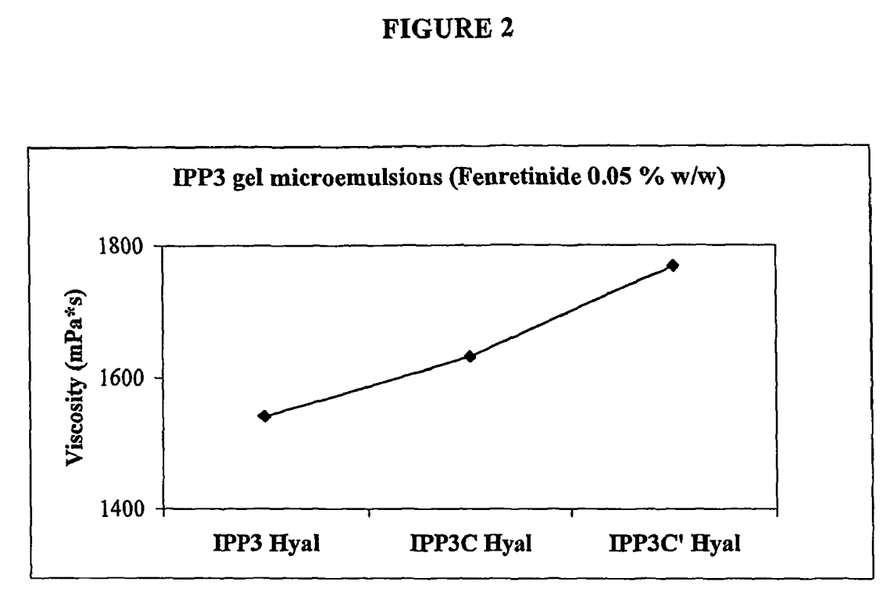
FIG. 2 shows the viscosity trend of gel microemulsions based on isopropyl palmitate (IPP) which have the same ratio [W]/[lec] (=3) and concentration as the drug fenretinide (0.05%), but a different qualitative/quantitative composition, and contain hyaluronic acid sodium salt.

FIG. 2 shows the viscosity trend of gel microemulsions based on isopropyl palmitate (IPP) which have the same ratio [W]/[lec] (=3) and concentration as the drug fenretinide (0.05%), but a different qualitative/quantitative composition, and contain hyaluronic acid sodium salt (Hyalastine fraction) as viscosity agent in order to obtain the viscosity and consistency characteristics considered ideal for the intended uses.

Figure 3:
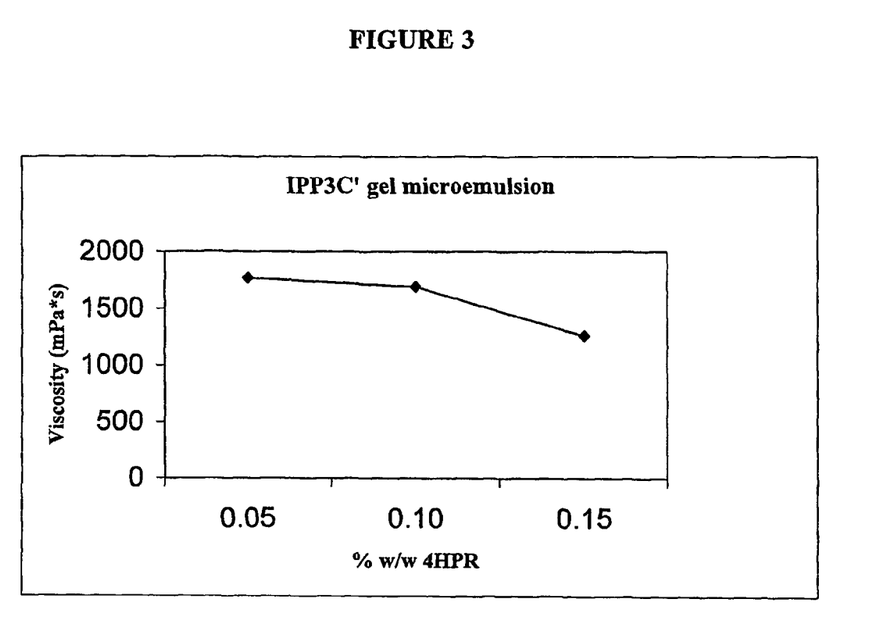
FIG. 3 shows the viscosity trend of the microemulsion designated as prototype IPP3C', according to the fenretinide concentration (4HPR).

FIG. 3 shows the viscosity trend of the microemulsion classed as prototype IPP3C', according to the fenretinide concentration (4HPR), in which slightly inferior viscosity and consistency characteristics are observed as the dose of fenretinide increases.

Example 5

Diffusion Kinetics of Fenretinide

An in vitro study was conducted to compare the diffusion or permeation (through a membrane) kinetics of fenretinide in the microemulsions according to the invention with fenretinide in conventional formulations, such as the "ointment base containing cetomacrogol" and "fatty cream base containing cetomacrogol" described in the Italian Official Pharmacopoeia (F.U.), current edition.

"Franz diffusion cells" associated with a cellulose membrane were used to study the diffusion kinetics of fenretinide in the different formulations.

The cell consists of two glass sections, one above the other. The inner diameter of the cell is 1 cm (equal to an area of 0.78 cm$^2$).

The formulation containing fenretinide was placed in the top section, while the bottom section was filled with the receptor phase constituted by methanol, and maintained under constant stirring by means of a magnetic "follower" fitted at the base of the cell.

The membrane, previously moistened with the receptor phase, was placed between the two sections. The two sections of the cell were assembled, taking care to avoid the formation of air bubbles. All the experiments were carried out under the same conditions: shaded from the light, at the temperature of 25° C., the bottom section being thermostated at 32° C., and 4 cells being used in parallel.

Samples of the receptor phase were taken at pre-set intervals (from 30 minutes to 8 hours) using a syringe with a flexible teflon tube; each sample was then replaced with an equal volume of receptor phase.

The samples were analysed for their fenretinide content using reverse-phase HPLC chromatography. The total quantities of fenretinide released per area unit ($\mu g/cm^2$) were calculated from the results of the chromatographic analysis.

The tests were repeated in quadruplicate for each formulation. The mean values were then calculated and shown in the graph as a function of time, expressed in hours.

The test points were interpolated with a linear regression calculation, obtaining lines of the type "y=mx+q". Angular coefficient "m", which represents the slope of the line, corresponds to test flow "Js".

It is known that Js=C×Jn, where C is the concentration of the drug expressed in mg/ml.

As the fenretinide concentration in all the formulations analysed was 1 mg/ml, "Js" is equal to "Jn". "Jn" represents the diffusion coefficient, namely the flow rate at which the drug permeates through the membrane.

Figure 4:
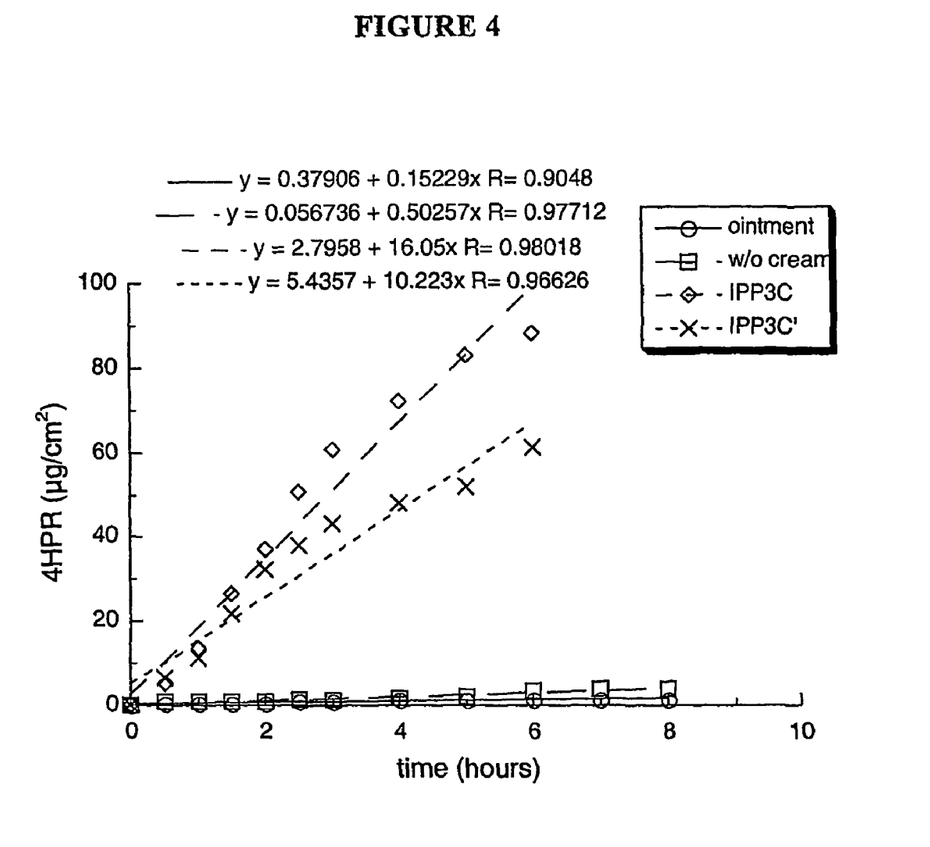
FIG. 4 shows the diffusion or permeation kinetics of fenretinide (absorption rate) in gel microemulsions IPP3C and IPP3C' (without hyaluronic acid sodium salt, Hyalastine fraction) by comparison with fenretinide in conventional formulations. The angular coefficients of the lines obtained represent the values of diffusion coefficient "Jn".

FIG. 4 shows the diffusion or permeation kinetics of fenretinide (absorption rate) in gel microemulsions IPP3C and IPP3C' (without hyaluronic acid sodium salt, Hyalastine fraction) by comparison with fenretinide in conventional formulations ("ointment base containing cetomacrogol" and "fatty cream base containing cetomacrogol"); the angular coefficients of the lines obtained represent the values of diffusion coefficient "Jn".

Figure 5:
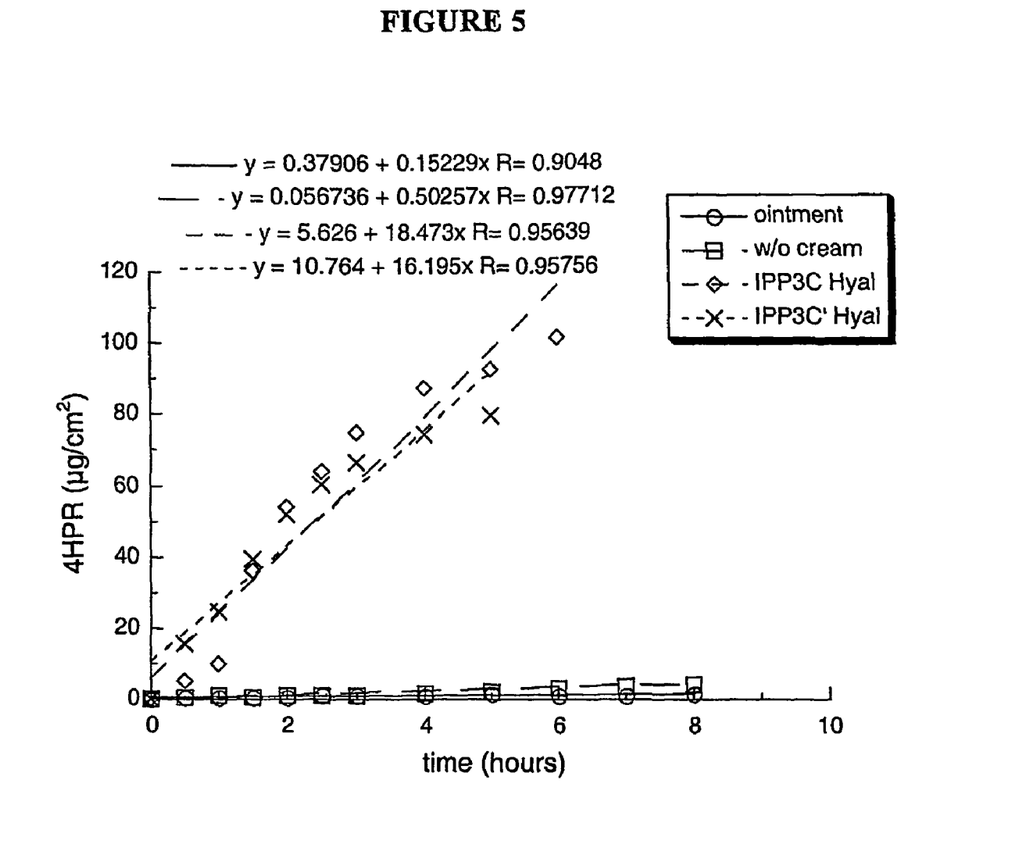
FIG. 5 shows the diffusion or permeation kinetics of fenretinide (absorption rate) in the same gel microemulsions containing hyaluronic acid sodium salt (Hyalastine fraction) by comparison with fenretinide in conventional formulations.

FIG. 5 shows the diffusion or permeation kinetics of fenretinide (absorption rate) in the same gel microemulsions containing hyaluronic acid sodium salt (Hyalastine fraction) by comparison with fenretinide in conventional formulations ("ointment base containing cetomacrogol" and "fatty cream base containing cetomacrogol").

Figure 6:
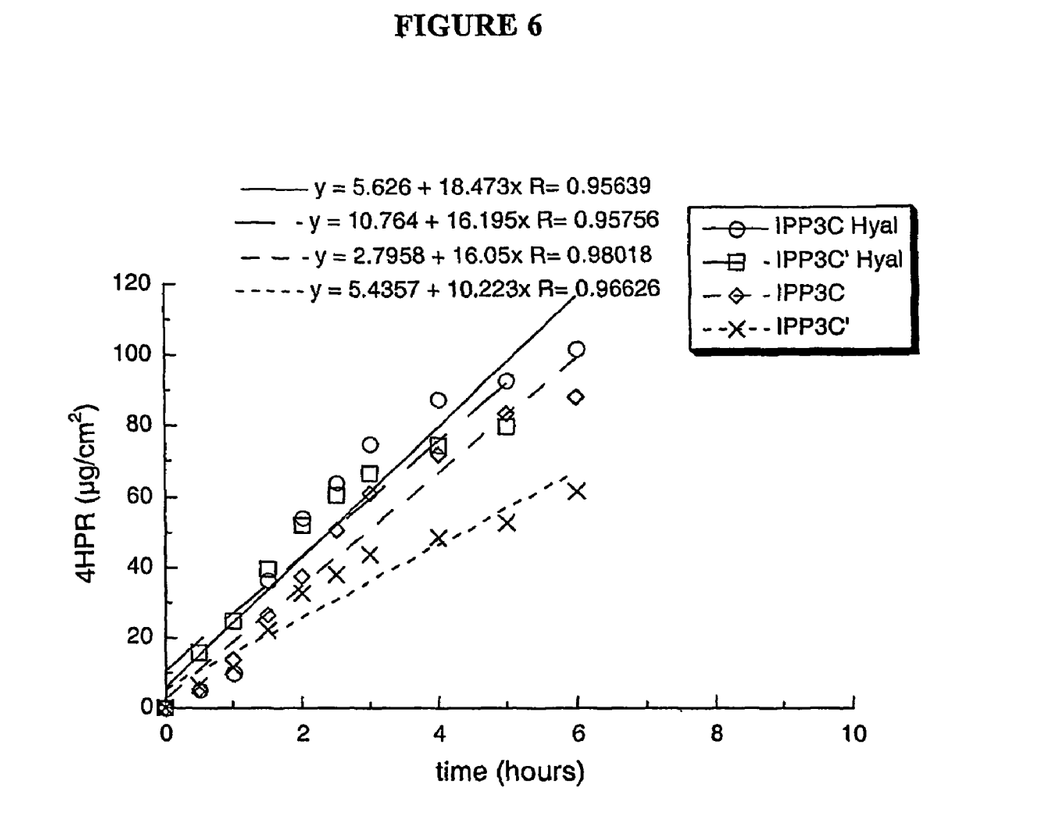
FIG. 6 shows the diffusion or permeation kinetics of fenretinide (absorption rate) in gel microemulsions IPP3C and IPP3C' with or without hyaluronic acid sodium salt (Hyalastine fraction).

FIG. 6 shows the diffusion or permeation kinetics of fenretinide (absorption rate) in gel microemulsions IPP3C and IPP3C' with or without hyaluronic acid sodium salt (Hyalastine fraction).

The diffusion (or permeation or absorption) coefficients "Jn" of fenretinide carried in gel microemulsions type IPP3 ([W]/[lec]=3), in the absence and presence of hyaluronic acid sodium salt (Hyalastine fraction), and in conventional formulations, are set out in the table below:

| Formulation | Fenretinide (% w/v) | $J_n$ ($\mu g/cm^2/h$) | log $J_n$ |
|---|---|---|---|
| Ointment base, F.U | 0.1 | 0.15 | −0.82 |
| W/O cream base, F.U. | 0.1 | 0.50 | −0.3 |
| IPP 3 C | 0.1 | 13.43 | 1.12 |
| IPP 3 C HYAL | 0.1 | 18.47 | 1.26 |
| IPP 3 C' | 0.1 | 10.22 | 1.00 |
| IPP 3 C' HYAL | 0.1 | 16.19 | 1.20 |

The following conclusions can be drawn from the test results obtained:

The kinetics of diffusion or permeation (absorption rate) of fenretinide carried as a gel microemulsion based on phospholipids (soy phosphatidylcholine) are considerably greater than those of the drug when carried in conventional formulations (W/O cream or ointment); the diffusion coefficients "Jn" of fenretinide carried as a gel microemulsion are considerably greater than those obtained with an ointment (approx. 79 times higher) and/or a W/O cream (approx. 24 times higher).

Surprisingly, the kinetics of diffusion or permeation (absorption rate) of fenretinide carried as a gel microemulsion based on phospholipids (soy phosphatidylcholine) are considerably increased by the presence in the formulation of hyaluronic acid sodium salt (Hyalastine fraction), which therefore has the effect of promoting percutaneous absorption.

The invention claimed is:

1. A water-in-oil microemulsion comprising a retinoid as active ingredient, a phospholipid emulsifier, and sodium hyaluronate, wherein:
   the aqueous phase is present at a concentration ranging from 0.5 to 2% by weight;
   the phospholipid emulsifier is phosphatidylcholine or soy lecithin, and is present in an amount ranging from 10 to 15% by weight;
   the sodium hyaluronate is a fraction having a molecular weight ranging from 50 to 200 kDa, and is present in an amount ranging from 0.001 to 0.01% by weight; and
   the molar ratio of water concentration to lecithin phospholipid emulsifier concentration (W/PE) is 3.

2. The microemulsion of claim 1, wherein the oil phase consists of alkyl esters of $C_{10}$-$C_{22}$ fatty acids.

3. The microemulsion of claim 2, wherein the oil phase consists of isopropyl palmitate.

4. The microemulsion of claim 1, wherein the retinoid is selected from the group consisting of isotretinoin (13-cis-retinoic acid), tazarotene and fenretinide.

5. The microemulsion of claim 4, wherein the retinoid is fenretinide.

6. The microemulsion of claim 1, further comprising at least one derivative of hyaluronic acid (HA) selected from the group consisting of:
   HA salts with organic and/or inorganic bases with a molecular weight of 50-730 KDa or a high molecular weight of 750-1230 KDa;
   esters of HA with alcohols of the aliphatic, araliphatic, cycloaliphatic, aromatic, cyclic and heterocyclic series;
   amides of HA with amines of the aliphatic, araliphatic, cycloaliphatic, aromatic, cyclic and heterocyclic series;
   0-sulphated HA derivatives up to the 4th degree of sulphation; and auto-crosslinked HA.

7. The microemulsion of claim 1, further comprising antioxidants and preservatives.

8. The microemulsion of claim 7, containing 4-tocopherol and parabens.

9. A pharmaceutical composition comprising the microemulsions of claim 1.

10. The microemulsion of claim 1, wherein the weight percentage of active ingredients is from 0.01% to 0.5% in weight.

11. The microemulsion of claim 1, wherein the sodium hyaluronate promotes percutaneous absorption of the water-in-oil microemulsion.

12. The microemulsion of claim 1, wherein the fraction of sodium hyaluronate having a molecular weight ranging from 50 to 200 kDa is hyalastine.

13. A method of preparing medicinal products with chemoprotective activity, which comprises adding an effective amount of the microemulsion according to claim 1 to an acceptable carrier.

14. A method for preparing the microemulsion of claim 1, which comprises the addition of a solution of phospholipid emulsifier in the oil phase to a retinoid solution in the same oil phase, and the subsequent addition of an aqueous solution.

15. The method of claim 14, wherein the aqueous solution comprises hyaluronic acid (HA), HA salts or HA derivatives thereof, preservatives, or EDTA, and the HA derivative is selected from the group consisting of:

HA salts with organic and/or inorganic bases with a molecular weight of 50-730 KDa or a high molecular weight of 750-1230 KDa;

esters of HA with alcohols of the aliphatic, araliphatic, cycloaliphatic, aromatic, cyclic and heterocyclic series;

amides of HA with amines of the aliphatic, araliphatic, cycloaliphatic, aromatic, cyclic and heterocyclic series;

0-sulphated HA derivatives up to the 4th degree of sulphation; and auto-crosslinked HA.

\* \* \* \* \*